(12) United States Patent
Witt et al.

(10) Patent No.: US 9,459,239 B2
(45) Date of Patent: Oct. 4, 2016

(54) INTAKE MONITORING FOR ACCURATE PROPORTIONING

(75) Inventors: Klaus Witt, Keltern (DE); Konstantin Choikhet, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1427 days.

(21) Appl. No.: 13/178,814

(22) Filed: Jul. 8, 2011

(65) Prior Publication Data

US 2013/0008523 A1     Jan. 10, 2013

(51) Int. Cl.
    *G05D 11/00*     (2006.01)
    *G01N 30/34*     (2006.01)

(52) U.S. Cl.
    CPC .......... *G01N 30/34* (2013.01); *Y10T 137/2499* (2015.04)

(58) Field of Classification Search
    USPC .................................. 73/61.55, 61.56, 61.52
    See application file for complete search history.

(56) References Cited

U.S. PATENT DOCUMENTS

| | | | |
|---|---|---|---|
| 4,018,685 A | | 4/1977 | Saunders et al. |
| 4,032,445 A | * | 6/1977 | Munk ........................... 210/103 |
| 4,043,906 A | * | 8/1977 | Helmer ......................... 210/659 |
| 4,128,476 A | | 12/1978 | Rock |
| 4,595,496 A | | 6/1986 | Carson |
| 4,624,625 A | | 11/1986 | Schrenker |
| 4,980,059 A | | 12/1990 | Barlow et al. |
| 4,982,597 A | | 1/1991 | Berger |
| 5,135,658 A | | 8/1992 | Lee et al. |
| 5,630,706 A | * | 5/1997 | Yang ................................ 417/3 |
| 5,755,559 A | * | 5/1998 | Allington et al. ............... 417/53 |
| 5,862,832 A | | 1/1999 | Victor et al. |
| 7,631,542 B2 | | 12/2009 | Weissgerber |
| 2006/0219618 A1 | * | 10/2006 | Witt et al. .................. 210/198.2 |
| 2007/0000313 A1 | * | 1/2007 | Weissgerber ................ 73/61.56 |
| 2008/0022765 A1 | * | 1/2008 | Witt et al. ........................ 73/199 |
| 2008/0080981 A1 | * | 4/2008 | Witt et al. ........................ 417/32 |
| 2009/0076631 A1 | * | 3/2009 | Witt et al. ........................ 700/14 |

FOREIGN PATENT DOCUMENTS

| | | |
|---|---|---|
| CN | 1168720 A | 12/1997 |
| EP | 0309596 A1 | 4/1989 |

(Continued)

OTHER PUBLICATIONS

Chinese Office Action dated Dec. 2, 2012.

*Primary Examiner* — Hezron E Williams
*Assistant Examiner* — Xin Zhong

(57) ABSTRACT

A fluid supply system configured for metering two or more fluids in controlled proportions, including a plurality of solvent supply lines, a pumping unit configured for taking in fluids from selected solvent supply lines and for supplying a pressurized mixture, a proportioning valve configured for modulating solvent composition by sequentially coupling selected ones of the solvent supply lines with the inlet of the pumping unit, a sensor configured for sensing process information in the fluid supply system, an analysis entity configured for analyzing the process information for determining reciprocating element related information at a beginning of fluid intake, and a control unit configured for switching the proportioning valve to sequentially couple selected ones of the solvent supply lines to the inlet of the pumping unit at one or more switching points based on the given metering scheme and based on the reciprocating element related information.

21 Claims, 3 Drawing Sheets

(56) References Cited

FOREIGN PATENT DOCUMENTS

| | | | |
|---|---|---|---|
| EP | 1577012 | A1 | 4/2005 |
| EP | 1724576 | A2 | 11/2006 |
| JP | 110509312 | A1 | 8/1999 |
| WO | 9604547 | A1 | 2/1996 |
| WO | 9701183 | A1 | 1/1997 |
| WO | 2004027535 | A1 | 4/2004 |
| WO | 2010030720 | A1 | 3/2010 |

* cited by examiner

INTAKE MONITORING FOR ACCURATE PROPORTIONING

The present invention relates to a fluid supply system, and to a method of operating a fluid supply system. The present invention further relates to a sample separation system, in particular in a high performance liquid chromatography application.

BACKGROUND

U.S. Pat. No. 4,018,685 discloses proportional valve switching for gradient formation. U.S. Pat. No. 4,595,496 discloses a liquid composition control for avoiding pump draw stroke non-uniformities. U.S. Pat. No. 4,980,059 discloses a liquid chromatograph. U.S. Pat. No. 5,135,658 discloses a coordinated chromatography system. U.S. Pat. No. 7,631,542 discloses a chromatography system with fluid intake management. U.S. Pat. No. 5,862,832 describes a gradient proportioning valve. International patent application WO 2010/030720 discloses a modulation of time offsets for solvent proportioning.

EP 1,724,576 discloses methods for operating a chromatography system. Specifically, methods for operating a pumping system within a chromatography system are disclosed. The methods presented are directed to pumping apparatus in which very small amounts of fluid are pumped through the system. A number of techniques for detecting and compensating for leaks are presented as well as a number of techniques for operating the pumping system.

U.S. Pat. No. 4,624,625 discloses that a high pressure metering pump has a duty cycle consisting of an aspiration portion where liquid is aspirated into a pumping chamber, a compression portion where the aspirated liquid is compressed to feed pressure, a feed portion where a part of the compressed liquid is expelled out of the pumping chamber, and a decompression portion where the liquid remaining in the pumping chamber is expanded to aspiration pressure. A measurement and control apparatus for the pump comprises a controller for adjusting and keeping constant the mean flow rate of the pumped liquid on the aspiration side or on the high pressure side of the pump. The apparatus further comprises a detector for detecting the transition point between the compression and feed portions and/or between the decompression and aspiration portions. The detector derives a control signal for the pump speed and for the optimal opening instant of an externally actuated input valve of the pump from the phase relationships of said transitions.

U.S. Pat. No. 4,128,476 discloses that in the cycle of a positive displacement LC pump system the output pressure is sensed to measure onset of output flow as a time lag from the beginning of the output stroke to give an estimate of the input filling time lag from the beginning of the fill stroke. This estimate is used to recompute a proportional module output for controlling the timing of a proportioning valve at the inlet to the LC pump so as to bring the actual operating conditions of the pump fill cycle into correspondence with the predetermined demanded ratios of the components either in isocratic or gradient program mode.

SUMMARY

There may be a need for supplying pressurized fluids with high accuracy.

According to an exemplary embodiment, a fluid supply system (particularly a liquid supply system) configured for metering two or more fluids (particularly liquids) in controlled proportions in accordance with a given (or a predetermined or a fixed) metering scheme and for supplying a resultant mixture is provided, the fluid supply system comprising a plurality of solvent supply lines, each fluidically connected with a fluid source (particularly a respective reservoir or a pipeline) providing a respective fluid, a pumping unit comprising a reciprocating element configured for displacing fluid supplied at an inlet of the pumping unit and for supplying the pressurized fluid at an outlet of the pumping unit, wherein the pumping unit is configured for taking in fluids from selected solvent supply lines and for supplying a pressurized mixture of the fluids at its outlet, a proportioning valve interposed between the solvent supply lines and the inlet of the pumping unit, the proportioning valve configured for modulating solvent composition by sequentially coupling selected ones of the solvent supply lines with the inlet of the pumping unit, a sensor configured for sensing process information in the fluid supply system relating to a fluid intake process of the pumping unit, an analysis entity configured for analyzing the sensed process information for determining (for instance exclusively) the event of the beginning of a fluid intake process, wherein the analysis entity is further configured for determining reciprocating element related information corresponding to the event of the beginning of the fluid intake process, and a control unit configured for switching the proportioning valve to sequentially couple selected ones of the solvent supply lines to the inlet of the pumping unit at one or more switching points (particularly switching points of time, more generally switching points during the operating cycle of the reciprocating element or one or more supply line switching events) based on the given metering scheme and based on the reciprocating element related information (particularly information about the motion of the reciprocating element).

According to another exemplary embodiment, a fluid supply system (particularly a liquid supply system) is provided which comprises a pumping unit comprising a reciprocating element configured for displacing a fluid (particularly a liquid) supplied at an inlet of the pumping unit and for supplying the pressurized fluid at an outlet of the pumping unit, a sensor configured for sensing process information in the fluid supply system relating to a fluid intake process of the pumping unit, and an analysis entity configured for analyzing the sensed process information for determining fluid intake information indicative of the beginning of the fluid intake process, wherein the analysis entity is configured for determining reciprocating element related information corresponding to the occurrence of the beginning of the fluid intake process.

According to yet another exemplary embodiment, a sample separation system for separating components of a sample fluid (particularly a sample liquid) in a mobile phase is provided, the sample separation system comprising a fluid supply system having the above-mentioned features, the fluid supply system being configured to drive the fluid as the mobile phase through the sample separation system, and a separation unit, preferably a chromatographic column, configured for separating components of the sample fluid in the mobile phase.

According to another exemplary embodiment, a method of operating a fluid supply system for metering two or more fluids in controlled proportions in accordance with a given metering scheme and for supplying a resultant mixture is provided, the fluid supply system comprising a plurality of solvent supply lines, each fluidically connected with a fluid source providing a respective fluid, wherein the method comprises controlling a pumping unit comprising a reciprocating element for displacing fluid supplied at an inlet of the pumping unit and for supplying the pressurized fluid at an outlet of the pumping unit, wherein the pumping unit takes in fluids from selected solvent supply lines and supplies a pressurized mixture of the fluids at its outlet, modulating solvent composition by a proportioning valve, which is interposed between the solvent supply lines and the inlet of the pumping unit, by sequentially coupling selected ones of the solvent supply lines with the inlet of the pumping unit, sensing process information in the fluid supply system relating to a fluid intake process of the pumping unit, analyzing the sensed process information for determining the event of the beginning of a fluid intake process, and determining reciprocating element related information at the event of the beginning of the fluid intake process, and switching the proportioning valve to sequentially couple selected ones of the solvent supply lines to the inlet of the pumping unit at one or more switching points (for instance once or more during the operating cycle of the pump/reciprocating element) based on the given metering scheme and based on the reciprocating element related information.

According to another exemplary embodiment, a method of operating a fluid supply system is provided, wherein the method comprises controlling a pumping unit comprising a reciprocating element for displacing a fluid supplied at an inlet of the pumping unit and for supplying the pressurized fluid at an outlet of the pumping unit, sensing process information in the fluid supply system relating to a fluid intake process of the pumping unit, analyzing the sensed process information for determining fluid intake information indicative of the beginning of the fluid intake process, and determining reciprocating element related information corresponding to the occurrence of the beginning of the fluid intake process.

According to still another exemplary embodiment of the present invention, a software program or product is provided, preferably stored on a data carrier, for controlling or executing any of the methods having the above mentioned features, when run on a data processing system such as a computer (for instance a portable computer, portable data processor or dedicated controller).

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of fluid supply control. The fluid supply control scheme according to an embodiment of the invention can be performed or assisted by a computer program, i.e. by software, or by using one or more special electronic optimization circuits, i.e. in hardware, or in form of program stored in non-volatile memory in controlling hardware, that is in form of embedded software, or in hybrid form, i.e. by means of combination of any of the above components. In other words, any implementation in software, firmware (embedded software) and/or hardware (for instance by an ASIC, application specific integrated circuit) is possible.

In the context of this application, the term "fluid" may particularly denote any liquid, any gas, any mixture of liquid and gas, optionally comprising solid particles. Particularly, analytes in liquid chromatography are not necessarily liquids, but can be dissolved solids or dissolved gases.

In the context of this application, the term "given metering scheme" may particularly denote a sequence of commands or instructions, optionally accompanied by one or more data or parameter sets, specifying a characteristic of a defined metering procedure with regard to the fluid mixture or solvent composition to be provided via the solvent supply lines and the proportioning valve to the pumping unit. Particularly, the metering scheme may define a chronology of the switching state of the partitioning valve and therefore the relative or absolute amounts of fluids supplied via the various solvent supply lines. When this metering scheme is given, it may be not freely modifiable so that at least a part of the metering scheme is to be applied and will not be changed upon synchronizing pumping unit and proportioning valve. However, the given metering scheme may be adjustable to a certain extent, i.e. it may be possible to cut out a portion of the metering scheme so that only this cut out portion is then applied. Examples for a metering scheme include a proportioning valve switching sequence within one piston cycle (which may to a certain degree be derived from an instruction or a set of instructions by processing of those in the pump), or a gradient program in accordance to which the partitioning valve provides a solvent composition changing in course of analysis according to a predefined program or scheme.

In the context of this application, the term "process information" may particularly denote any measured sensor data being indicative of the process of metering two or more fluids in controlled proportions, particularly being indicative of the fluid intake process and more particularly indicative of the beginning of the fluid intake process. More specifically, the process information may relate to detected parameters, such as flow rate value, pressure value or any other measureable parameter indicative of a motion of fluid through the system or of the change of the fluid state between quiescence and motion.

In the context of this application, the term "fluid intake process" may particularly denote the procedure during which the fluid supplied via the solvent supply lines is intaken or sucked in by the pumping unit, i.e. is introduced into a pumping chamber. During the reciprocation motion of the reciprocating element, different phases may be distinguished starting from aspiration of fluid, compression of the fluid, and expelling the fluid under pressure. The fluid intake process specifically relates to the aspiration of fluid as delivered by the proportioning valve to the pumping unit.

In the context of this application, the term "event of the beginning of the fluid intake process" may particularly denote that mere occurrence of the initiation of the fluid intake process by the reciprocating element is identified. In other words, is it detected merely the fact that the fluid intake process has started at a certain point of time. Hence, for the purpose of determining of beginning of the fluid intake process, no quantitative analysis of the sensed data is necessary but in contrast to this merely the qualitative information that an event of the beginning of the fluid intake process has been detected needs to be derived. However, this does not exclude that the sensor data is analyzed quantitatively for other purposes such as monitoring. For example, it may be convenient to perform a quantitative analysis in order to derive the event or even to recalculate or re-estimate back the exact condition (time, piston position, motion phase, etc.) corresponding to the occurrence of the event. However the quantitative output of the absolute sensed values is not necessary. On the other hand these might be used also for diagnostic purposes, such as sensing of the fluid level in the supply, sensing of the state of the inlet filter, state or leak in the valves, etc.

In the context of this application, the term "reciprocating element related information" may particularly denote any data or information, which correlates the detected event of the beginning of the fluid intake process with an assigned operation state of the reciprocating element at that point of time. Particularly, the reciprocating element related information may define at which spatial position or in which operational condition during a duty cycle the reciprocating element is or has been at the point of time of the beginning of the fluid intake process. Alternatively, the reciprocating element related information may define time shift or phase information at the point of time of the beginning of the fluid intake process relative to a reference point during a duty cycle of the reciprocating element. Therefore, a correlation between the sensed existence of the event on the one hand and a reciprocating element configuration on the other hand may be indicated by the reciprocating element related information.

The "analysis entity" may be implemented in hardware, in software, or in hybrid form, i.e. having hardware and software components. For instance, the analysis entity may be a separate analysis unit (such as a separate processor) or may form part of the control unit (which may also be or be part of a separate processor). It is however also possible that the analysis entity is an analysis algorithm or process included or embedded into the control unit. For instance, the analysis entity may be program code, for example in firmware.

According to an exemplary embodiment of the invention, a control scheme for a fluid supply system is provided, which is based on the consideration that an actual relation between a performance of a reciprocating element in a pumping unit on the one hand and a switching sequence of a proportioning valve on the other hand is not always well-known and might deviate from a supposed or desired target relation. In reality, artifacts such as leaks, compressibility of liquid under high pressure, temperature effects, hardware elasticity, aging effects or the like may result in a deviation between an actual cooperation of pumping unit and proportional valve and an ideal target behavior, i.e. an idealized way of cooperating. Such a deviation may adversely affect precision and/or accuracy of the metering of fluid, and therefore precision and/or accuracy of an application of the metered fluid such as a chromatographic separation. An embodiment of the invention faces this challenge by detecting the event of the initiation of a fluid intake process and by using this sensed information to derive corresponding information with regard to the actual behavior or status of the reciprocating element. Therefore, only the beginning of the fluid intake process of the pumping unit and a corresponding status of the reciprocating element needs to be detected, determined, recognized or identified, since this information can be used to adjust operation of the fluid supply system, while fully maintaining or basically maintaining a predefined or predetermined metering scheme or at least a part thereof. In other words, the sensor information will preferably be used for the purpose of deriving timing, duty cycle phase, or position information with regard to the beginning of the intake process in terms of corresponding reciprocating element position, while the sensed information may be disregarded for other purposes. Therefore, embodiments of the invention may still benefit from a properly defined and accurate metering scheme, while only adapting a synchronization or timing between operation of the pumping unit and the proportioning valve.

Thus, the concept of a metering pump may be followed without the need of measuring the flow value or another parameter in absolute values. Particularly, in case of a varying fluid composition, the metering concept is considered more reliable than the quantitative signal of a flow sensor, which is typically composition dependent. Therefore, in exemplary embodiments of the invention it is sufficient to use the sensor information for detecting the state or event of the beginning of the fluid intaking process rather than for extraction of quantitative description of the fluid movement. From this point of time onwards, such an embodiment of the invention trusts the corresponding precise metering scheme, while not necessarily using the sensor signals to a further extent for control purposes or the like.

When fluids are multiplexed in a proportioning valve and the mixture is brought to a high pressure in a pumping unit, it would be desirable to precisely know a correlation between the multiplexer cycle and the position of the reciprocating element such as a piston within a pumping chamber on one side and the fluid motion on the other side. In reality this is however not the case in many scenarios so that it is frequently unknown, at which point of time an actual intake process begins and ends. In view of this uncertainty concerning the point of time at which the actual intake process starts (which is important since this point of time defines the volume of the intaken packet of fluid), it is advantageous that exemplary embodiments of the invention can determine the start of the intake process for instance by a sudden change of a fluid motion in the fluid supply system. The information regarding the point of time, at which the intaking process starts, can be correlated to a certain piston position, so that a correct composition of fluids can be adjusted. As a mere example, if the metering procedure is late by for instance 2 µl in a process in which altogether 40 µl solvent shall be supplied, this fluid supply system can be correspondingly controlled in accordance to the fact, that only 38 µl are being delivered. Thus the information can be provided to the controlling system timely, so that either the volumes of the individual packets are scaled properly or the total intake volume is extended or other corrective measures are taken. Taking this measure allows at the same time to compose the solvent correctly and to know precisely which amount of solvent has been delivered.

In the following, further exemplary embodiments of the fluid supply systems will be explained. However, these embodiments also apply to the liquid separation system, the methods, and the software program or product.

In an embodiment, the control unit is configured for switching the proportioning valve using the given metering scheme and based on the reciprocating element related information for synchronizing a proportioning valve duty cycle with a pumping unit duty cycle. In this context, the term "duty cycle" (or working cycle or cycle of operation) may denote a sequence of tasks executed by the respective member. The duty cycle of the proportioning valve and the duty cycle of the pumping unit need to be matched so that they cooperate properly to enable the desired duty cycle of the fluid motion. In other words, when determining a lack of synchronization between the timing of the duty cycles of pumping unit and fluid motion relative to one another (for instance the pumping unit is considered to be already intaking the fluid, while in reality the fluid is not in motion yet), system operation may be adjusted so as to correct the timing of pumping unit and proportioning valve in accordance to one another so as to provide the desired motion duty cycle. However, during the synchronization, at least a part of the metering scheme may be maintained and applied unamended. Therefore, at least a section of the metering scheme may remain as it is during the control. In contrast to this, the coordination of the pump cycle and the switch cycle may be adjusted. For instance, upon determining that 2 µl solvent contribution of 40 µl total solvent is already expected to be intaken although the intake motion is just starting now, only a section of the metering scheme relating to the remaining 38 ml may need to be adjusted so that phasing of the pumping unit and the proportioning valve during the rest of the duty cycle stays unaffected.

It is hence possible to synchronize the proportioning valve with the piston which may both be controlled by the same control unit. It may however be even more challenging that another uncertainty is that due to hydraulic processes (e.g. thermal processes, decompression, volume contraction) the fluid movement is not synchronized with the piston movement. There is certain prognosis and calculated compensation for some of the effects in advance in the synchronization (e.g. for decompression) possible, but the other effects can still cause some discrepancy between the desired motion duty cycle and the actual one. It can then be advantageous to adjust the mutual timing of the proportioning valve and the piston to correct or account for these discrepancies.

In an embodiment, during an intake movement of the reciprocating element, when fluid is drawn in via the inlet of the pumping unit, the proportioning valve performs switching between different solvent supply lines. Therefore, fluid mixing can be performed by switching during the intaking process. It is also possible that, between intervals during which the fluid is drawn in via the inlet of the pumping unit, the proportioning valve performs switching between different solvent supply lines. Hence, the switching may even be performed in time intervals during which the fluid rests.

In an embodiment, the proportioning valve has a plurality of switching valves, with the switching valves being sequentially actuated during an intake movement of the reciprocating element of the pumping unit. Each of the switching valves may be formed by two switching members, i.e. a stator and a rotor, being rotatable relative to one another for switching.

In an embodiment, the proportioning valve is configured for selecting a selected one of the solvent supply lines corresponding to a multiplexer scheme. In this context, the term "multiplexer" may denote that, at a time, always one of multiple switching valves is coupled to the pumping unit. A multiplexer selects one of several input fluid flows and forwards the selected input fluid flow into a single output fluid flow. It is particularly possible to connect two valves in parallel with two sources of the same solvent and to switch the valves simultaneously or in an overlapping manner. This may be advantageous since the flow through two valves may have desirable properties so that it may be appropriate to allow the two valves to be opened at the same time.

In an embodiment, predefined portions of an intake movement of the reciprocating element are assigned to different solvents that are drawn in into the pumping unit, wherein proportioning is done by metering of one of volumetric packets, time slices, and position of the reciprocating element. In this context, a volumetric packet may define a fluid having a defined volume. The term "time slices" may denote certain defined time intervals which define a single phase within a reciprocating element's duty cycle which then, given a defined motion pattern of the reciprocating element, translates into a defined intake volume portion. The position of the reciprocating element in a pumping chamber at the beginning of an intake process as compared to a reference position (for instance a reverse point in a pumping chamber) may also be used as a measure for a fluid amount to be metered.

In an embodiment, the sensor is arranged, for instance, at a position between the proportioning valve and the pumping unit, or at a position in the solvent supply lines, or at a position within the proportioning valve, or at a position (particularly directly) upstream of an intake check valve arranged directly upstream of the pumping unit. It has turned out to be particularly advantageous that the position of the event detection sensor is between the proportioning valve and the pumping unit, since this is a spatial region in which the influence of the start of the intake process on the fluid properties of the fluid is particularly strong. However, also a position in the supply lines may be advantageous, since it allows to consider an impact on the individual components of the solvent composition as well. A position of such a sensor directly in a pumping chamber, in which the reciprocating element reciprocates allows for a very direct and hence precise measure of the beginning of the fluid intake process, albeit the mechanical requirements to such a sensor are much higher.

In an embodiment, the control unit is configured for coordinating operation of the pumping unit and the proportioning valve for at least partially compensating for a potential discrepancy between an actual relationship between operation of the pumping unit and the proportioning valve on one side and actual fluid motion on the other side, as indicated by the determined reciprocating element related information, and a target relationship between operation of the pumping unit and the proportioning valve on one side and fluid motion on the other side, as predefined for operating the fluid supply system. In this context, the term "actual relationship between operation of the pumping unit and the proportioning valve on one side and actual fluid motion on the other side" may particularly denote the real way how these components work together, usually in a non-ideal manner due to the occurrence of artifacts, such as leakage or the like. The term "target relationship between operation of a pumping unit and the proportioning valve" may particularly denote a desired interaction between these components as defined as an ideal operation mode, for instance an ideal chromatographic method. The sensing and analysis scheme according to an exemplary embodiment of the invention reduces lacking information with regard to a correlation between reciprocating element status and switching performance of the proportioning valve on one side and actual fluid motion on the other side. This addition item of information allows the control unit then to properly coordinate operation of reciprocating element and proportioning valve as the two actively controlled fluidic components. Comparing target and real operation modes to one another allows the control unit to perform a specific modification of the operation of the system so as to at least partially compensate for differences between real and target operation mode.

In an embodiment, the control unit is configured for controlling operation of the fluid supply system, particularly for controlling operation of the pumping unit, in accordance with the sensed process information, fluid intake information relating to the event of the beginning of the fluid intake process and/or the reciprocating element related information. The term "fluid intake information" may relate to any information with regard to the fluid intake process. The control operation may for instance be a temporal shift of a beginning of a duty cycle of the metering scheme and/or a cutout of a portion of the duty cycle of the proportioning valve so as to coordinate proportioning valve action and pumping unit action into so as to decrease or even minimize the discrepancy between actual and target operation modes.

In an embodiment, the control unit is configured for controlling fluid intake by the pumping unit based on the reciprocating element related information to adjust a size of fluid packets taken in by the pumping unit, particularly to adjust a size of a first fluid packet to be taken in during the intake process. The size of the fluid packets may be defined by an interval during which a certain solvent supply line is in fluid communication with the pumping unit due to a corresponding switching state of the proportioning valve. In an embodiment, the control unit is configured for controlling fluid intake by the pumping unit based on the reciprocating element related information to enable accuracy of or to correct a size of fluid packets taken in by the pumping unit. In an embodiment, the control unit is configured for controlling fluid intake by the pumping unit based on the reciprocating element related information to adjust a size of a first fluid packet to be taken in during the intake process in accordance with its relation to the size of other packets. Thus, while the metering scheme is generally maintained, size of individual fluid packets may be adjusted.

In an embodiment, the control unit is configured for controlling operation of the fluid supply system for at least partially compensating a potential discrepancy between target reciprocating element related data and the determined reciprocating element related information. Such a discrepancy may be a detected deviation between a desired behavior (for instance a desired or target position of the reciprocating element within the pumping unit corresponding to a certain event such as the beginning of a fluid intake process) and a real behavior (for instance an actual or real position corresponding to that event) of the pumping unit. Such a discrepancy can be reduced or eliminated by considering the information about a desired reciprocating element state at the beginning of the fluid intaking process as compared to a real one. However, it is also possible to model, simulate or predict the processes within the fluid supply system for a reduction of such a discrepancy.

In an embodiment, the control unit is configured for adjusting, based on the determined reciprocating element related information, a future motion profile in accordance with which the reciprocating element is moved in the pumping unit. For instance, it can be determined for the next or the following operation cycles as to how the operation of the proportioning valve and/or the pumping unit should be.

In an embodiment, the sensor comprises a pressure sensor, a flow sensor, temperature sensor, acoustic sensor, acceleration sensor, or any sensor capable of sensing a change in fluid flow properties of the fluid. It is understood that the begin of a fluid intake process goes along with a change of the fluid flow properties of the fluid in the corresponding conduit or channel, since a beginning of the fluid intake process will result in a sudden motion of the fluid. Therefore, any sensor being sensitive to such a change in the fluid flow can be used.

In an embodiment, the fluid supply system comprises a plurality of sensors arranged at different positions in the fluid supply system. Each of the sensors may detect process information indicative of the intake initiation. Particularly, at least one sensor may be arranged at a position between the proportioning valve and the pumping unit, and at least one other sensor may be arranged at a position in at least one of multiple solvent supply lines. It has turned out to be advantageous to provide not only a single sensor for the control scheme according to exemplary embodiment of the invention, but to foresee multiple sensors providing complementary information. This may allow to significantly refine the control architecture, since different sensors at different positions, optionally using different sensor types (such a pressure sensor, flow sensor, etc.), may be sensitive to different effects or artifacts. For instance, a leak in a solvent supply line can be precisely detectable by a sensor which is positioned directly in this solvent supply line. Artifacts resulting from compressibility of liquid will be the larger, the larger the pressure at a certain position is. These examples show that the use of complementary sensors, i.e. sensors providing independent, non-redundant information can improve the accuracy of the fluid intake monitoring.

In an embodiment, the reciprocating element related information is indicative of one of reciprocating element state information, process state information, time information, a spatial position of the reciprocating element within a pumping chamber of the pumping unit at the beginning of the fluid intake process, and a point of time at which the fluid intake process begins. More generally, reciprocating element related information may be information which allows to correlate the actual point in a duty cycle of the reciprocating element to the start of the fluid intake process.

In an embodiment, the analysis entity is configured for analyzing a course of a pressure trace, particularly a first derivative of a time-dependent pressure trace, as the sensed process information for determining the reciprocating element related information. The analysis entity may be further configured for determining the reciprocating element related information based on a position of a peak value, particularly a maximum value or a minimum value, of the course of the pressure trace. The term "course of a pressure trace" may particularly denote the time dependence of a pressure value as detected by a sensor in the fluid supply system. The start of an intake process may be detectable by certain feature such as e.g. a peak (i.e. a minimum value or maximum value) in such a pressure pattern, further on referred to as "specific feature", which can be determined in a highly precise manner when monitoring the first derivative of the pressure curve (wherein also the second derivative may provide valuable information).

In an embodiment, the analysis entity is configured for analyzing the sensed process information in terms of at least one predefined artifact criterion for determining at least one artifact feature in the sensed process information, and is configured for analyzing a relation between the at least one predefined artifact feature and the determined reciprocating element related information. Examples for the at least one predefined artifact criterion comprise an influence of gas bubbles in the fluid, an influence of leakage in the fluid supply system, an influence of compressibility of the fluid, a volume contraction resulting from mixing of two or more components of the fluid, an influence of a temperature of the fluid, and an influence of adiabatic expansion of the fluid. An experimentally identified discrepancy between real and target behavior of pumping unit may be analyzed in terms of a model of the physical processes within the fluid supply system, thereby allowing to suppress or even eliminate mathematically or numerically the impact of such artifacts on a measurement result such as a chromatogram. For instance, gas bubbles in the fluid may shift a specific feature (indicating beginning of a fluid intake process) in the pressure trace to higher values. A leakage in the system may shift such a specific feature in the pressure trace to lower values. In contrast to this, compressibility of the fluid will result in a shift of the specific feature in the pressure trace to the opposite position, i.e. to higher values. Also the temperature may have an impact on the point of time, at which a specific feature appears. These and/or other influences on the system behavior may be modeled and may be quantitatively considered for controlling the system to at least partially eliminate an undesired influence on the synchronization between partitioning valve and pumping unit.

In an embodiment, the pumping unit comprising a further reciprocating element configured for displacing, in cooperation with the reciprocating element, the fluid supplied at the inlet of the pumping unit and for supplying the fluid further pressurized at the outlet of the pumping unit. In this embodiment, more than one reciprocating element, for instance two pistons, may reciprocate in one and the same pumping chamber. The multiple reciprocating elements may all be controlled as described above for the case of a single reciprocating element only.

In an embodiment, the fluid supply system comprises a further pumping unit arranged downstream of the pumping unit and configured for displacing, by a further reciprocating element, the fluid supplied at the outlet of the pumping unit and at an inlet of the further pumping unit and for supplying the fluid further pressurized at an outlet of the further pumping unit. In this embodiment, several pumping units with individual reciprocating elements and chambers may be provided. For instance, multiple pumping units may be hydraulically coupled in series. The multiple pumping units may all be controlled as described above for the case of a single pumping unit only.

In an embodiment, the reciprocating element comprises a piston, a membrane, or may be configured as a pressure chamber. However, other embodiments of the reciprocating element are possible as well as long as the reciprocating element is capable of reciprocating within the pumping chamber resulting in reciprocating changes of the volume available to fluid within chamber.

In the following, further exemplary embodiments of the sample separation system will be explained. However, these embodiments also apply to the fluid supply systems, the methods, and the software program or product.

According to embodiments of the present invention, the fluid (particularly liquid) separation system further comprises at least one of: a sample injector configured to introduce the sample into the mobile phase; a detector configured to detect separated components of the sample; a collection unit configured to collect separated components of the sample; a data processing unit configured to process data received from the liquid separation system; a degassing apparatus for degassing the mobile phases; a separating unit such as a chromatographic column for separation of the sample components.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.agilent.com—which shall be incorporated herein by reference).

One embodiment of an HPLC system comprises a pumping apparatus having a piston for reciprocation in a pump working chamber to compress liquid in the pump working chamber to a high pressure at which compressibility of the liquid becomes noticeable, and to deliver said liquid at high pressure.

One embodiment of an HPLC system comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (e.g. from the supply), thus allowing to provide a continuous flow at the output. However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column providing the stationary phase. The column might be a glass or steel tube (e.g. with a diameter from 10 $\mu$m to 10 mm and a length of 1 cm to 1 m) or a microliquidic column (as disclosed e.g. in EP 1577012 A1 or the Agilent 1200 Series HPLC-Chip/MS System provided by the applicant Agilent Technologies, see e.g. http://www.chem.agilent.com/Scripts/PDS.asp ?1Page=38308). The individual components are retained by the stationary phase differently and separate from each other while they are propagating at different speeds through the column with the eluent. At the end of the column they elute separately, more or less one at a time. During the entire chromatography process the eluent might be also collected in a series of fractions. The stationary phase or adsorbent in column chromatography usually is a solid material. The most common stationary phase for column chromatography is surface modified silica gel, followed by silica gel and alumina. Cellulose powder has often been used in the past. Known are ion exchange chromatography, reversed-phase chromatography (RP), normal phase chromatography, hydrophilic interaction chromatography, size exclusion chromatography, affinity chromatography, etc. The stationary phases are usually fine powders or gels and/or the particles can be partially or entirely meso- and/or microporous providing extended surface area. Furthermore, there also exist monolithic columns comprising continuous porous stationary phase body for fast high performance liquid chromatography separations.

The mobile phase (or eluent) can be either a pure solvent or a mixture of different solvents. It can be chosen e.g. to adjust the retention of the components of interest and/or to minimize the amount of mobile phase to run the chromatography. The mobile phase can preferably been chosen so that the different components can be separated and/or isolated effectively. The mobile phase might comprise an organic solvent like e.g. methanol or acetonitrile, preferably diluted with water. For gradient operation water and organic solvent may be delivered from separate supply lines or reservoirs, from which the gradient pump delivers a programmed blend to the system. Other commonly used solvents may be isopropanol, tetrahydrofuran (THF), hexane, ethanol or other organic or inorganic liquid components and/or any combination thereof or any combination of these with aforementioned solvents.

The sample liquid might comprise any type of process liquid, natural sample like juice, body liquids like plasma or it may be the result of a reaction like from a fermentation broth.

The fluid is preferably a liquid but may also be or comprise a gas and/or a supercritical liquid (as e.g. used in supercritical liquid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

The HPLC system might further comprise a sampling unit for introducing the sample liquid into the mobile phase stream, a detector for detecting separated components of the sample liquid, a fractionating unit for dispatching or collecting fractions containing separated components of the sample liquid, or any combination thereof. Further details of HPLC system are disclosed with respect to the aforementioned Agilent HPLC series, provided by the applicant Agilent Technologies, under www.agilent.com which shall be in incorporated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs. The illustration in the drawing is schematic.

Figure 1A:
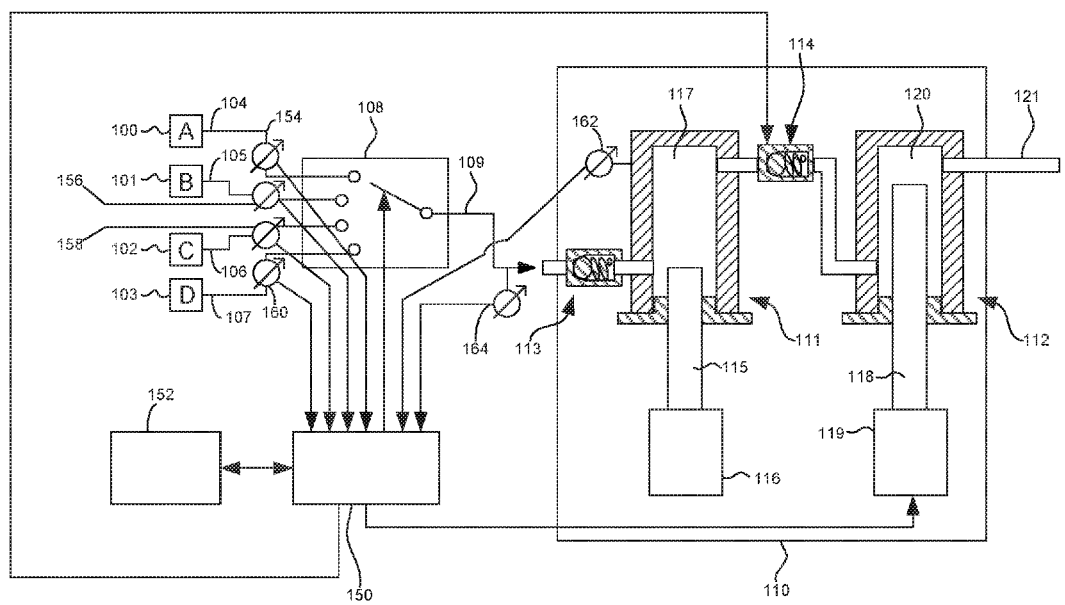
FIG. 1A shows part of a liquid separation system configured for supplying a flow of composite solvent.

The illustration in the drawing is schematic.

DETAILED DESCRIPTION

FIG. 1A shows a liquid supply system configured for metering liquids in controlled proportions and for supplying a resultant mixture. The liquid supply system comprises four reservoirs 100, 101, 102, 103, with each of the reservoirs containing a respective solvent, A, B, C, D. Each of the reservoirs 100 to 103 is fluidically connected via a respective liquid supply line 104, 105, 106, 107 with a proportioning valve 108. The proportioning valve 108 is configured to connect a selected one of the four liquid supply lines 104 to 107 with a supply line 109, and to switch between different liquid supply lines. The supply line 109 is connected with an inlet of a pumping unit 110. Hence, solvent metering is performed at the low-pressure side of the pumping unit 110.

In the example shown in FIG. 1A, the pumping unit 110 comprises a first piston pump 111 fluidically connected in series with a second piston pump 112. The first piston pump 111 is equipped with an inlet valve 113 and with an outlet valve 114. A first piston 115 is driven by a first motor 116 and reciprocates within the first pump chamber 117. A second piston 118 is driven by a second motor 119 and reciprocates within a second pump chamber 120. Alternatively, both pistons 115, 118 can be operated by a common drive system, e.g. a differential drive or gear.

During an intake phase of the first piston pump 111, the inlet valve 113 is open, the outlet valve 114 is closed, and the first piston 115 moves in the downward direction. Accordingly, solvent supplied via the supply line 109 is drawn into the first pump chamber 117. During the downward stroke of the first piston 115, the proportioning valve 108 may switch between different liquid supply lines and hence between different solvents. Thus, during the downward stroke of the first piston 115, different solvents may be drawn into the first pump chamber 117 one after the other. In an alternative construction, there may be individual inlet valves for each liquid supply line 104 to 107, which then are controlled like and instead of proportioning valve 108.

As can be further taken from FIG. 1A, a plurality of flow sensors are arranged in the liquid supply system. A first flow sensor 154 is arranged in first liquid supply line 104. A second flow sensor 156 is arranged in second liquid supply line 105. A third flow sensor 158 is arranged in third liquid supply line 106. A fourth flow sensor 160 is located within fourth liquid supply line 107. Each of the flow sensors 154, 156, 158 and 160 is capable of measuring the flow rate of the individual liquid in the respective individual liquid supply line 104 to 107 or at least to distinguish between the motion and quiescence state of the liquid. A fifth flow sensor 164 is located in a flow path between the proportioning valve 108 and check or inlet valve 113. Moreover, an additional sensor 162 (such as a pressure, temperature or similar sensor) can be arranged in a pumping chamber of the first piston pump 111. As an alternative to this flow sensor arrangement, it is also possible to substitute them partially or entirely by pressure sensors or the like.

The various sensors 154, 156, 158, 160, 162 and 164 each capture process information in the form of the measurement values over time. These sensor signals may be supplied directly from the flow sensors 154, 156, 158, 160, 162, 164 to a processor 150. The processor 150 can comprise a central processing unit, microprocessor or the like. Furthermore, the processor 150 is bidirectionally coupled for data communication with an input/output unit 152. Via the input/output unit 152, which may be a user interface, a user may input control commands to the fluid supply system, may monitor control information via a display or the like. As will be described in the following referring to FIG. 1B, the various sensor signals can be evaluated by the processor 150 so as to improve accuracy of the operation of the liquid supply system of FIG. 1A.

Figure 1B:
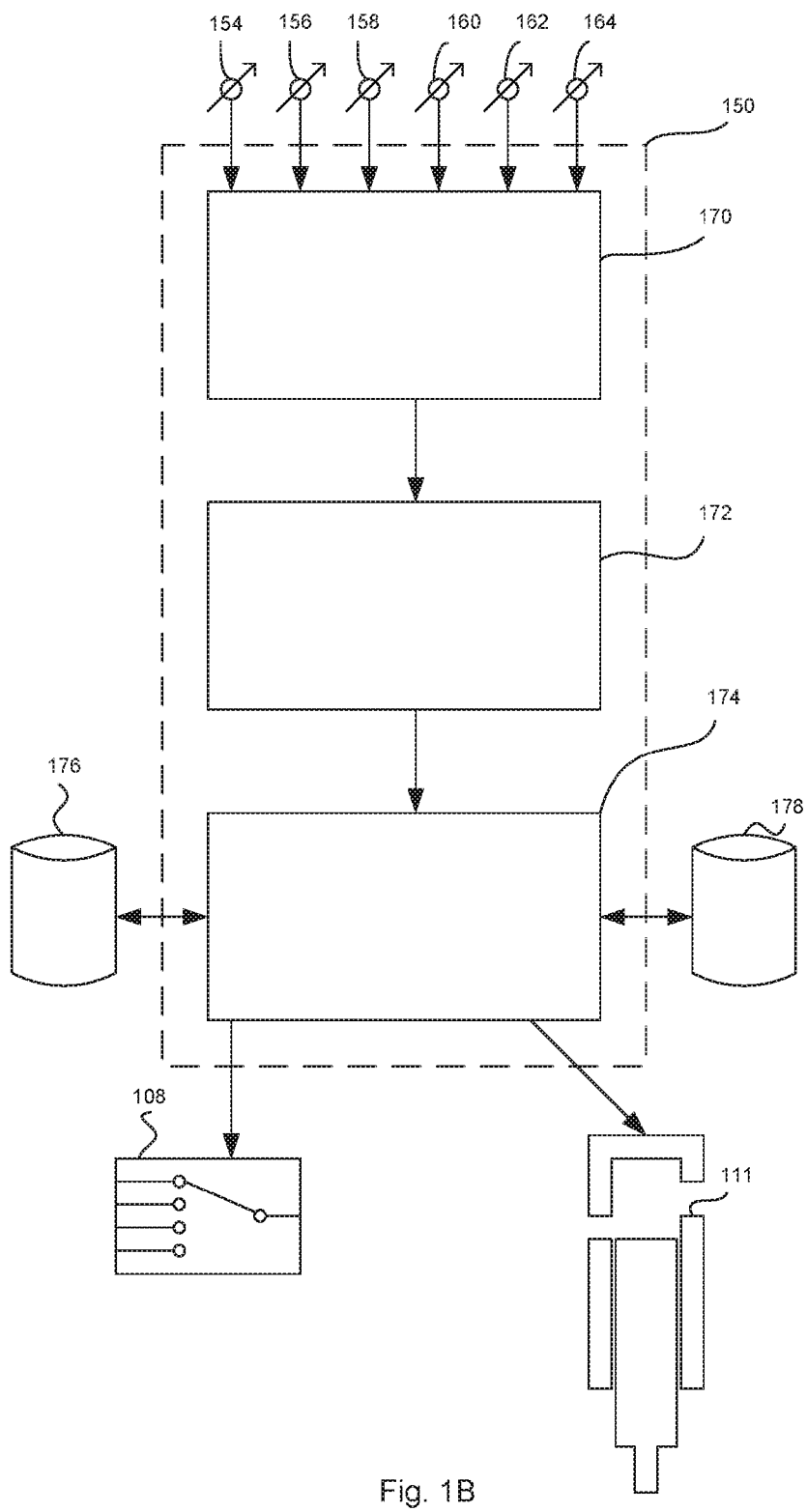
FIG. 1B shows details of a control block of the liquid separation system of FIG. 1A.

As can be taken from FIG. 1B illustrating details regarding the processor 150, the sensor signals as captured by the sensors 154, 156, 158, 160, 162, 164 are supplied to a first analysis entity 170 of the processor 150. The first analysis entity 170 is configured for analyzing the sensor signals for the mere purpose of determining the event of the beginning of a fluid intake process at the first piston pump 111. In other words, it is sufficient to capture very basic or simple sensor data by the flow sensors 154, 156, 158, 160, 162, 164, since the only necessary information derived by the first analysis entity 170 is the event when the starting of the fluid intake process occurs at the first piston pump 111. Upon having determined that event of liquid intake beginning (i.e. the moment at which fluid upstream of or in the inlet valve 113 starts its motion towards the first pump chamber 117), this information is supplied to a second analysis entity 172. While the analysis entities 170 and 172 are shown as separate blocks in FIG. 1B, they can also be realized as one and the same block, or as a separate processor. In the shown embodiment, the analysis entities 170 and 172 form part of processor 150.

The second analysis entity 172 is configured for determining piston related information at the point of time, at which the fluid intake process begins. Thus, the piston related information may correlate a characteristic or property of the first piston 115 (for instance the spatial position of the reciprocating first piston 115 within the first pump chamber 117) with the event that the fluid intake procedure at the first piston 115 has started. In other words, the second analysis entity 172 determines in which actual position the first piston 115 is at the beginning of the liquid intake process.

FIG. 1B furthermore shows a control unit 174 also forming part of the processor 150. The control unit 174 receives the data resulting from the analysis executed by the second analysis entity 172 and is configured for switching the proportional valve 108 to sequentially couple selected ones of the solvent supply lines 104 to 107 to the inlet of the pumping unit 110 at one or more switching points of time. This control of the proportioning valve 108 is performed based on a combination of two pieces of information. Firstly, the liquid supply system relies on a predefined metering scheme according to which the proportioning valve 108 meters the liquids. This data can be taken from a metering scheme database 176 storing parameter values and commands which define the given metering scheme. This metering scheme is used by the control unit 174 for operating proportioning valve 108. Secondly, the control unit 174 considers, as a basis for the controlling, the determined piston related information at the point of time of the fluid intake procedure, as received from the second analysis entity 172. The control unit 178 then determines an actual relationship between the liquid motion on one side and the duty cycles of the proportioning valve 108 and the first piston pump 111 on the other side, particularly in which condition the first piston pump 111 in fact is at the beginning of the liquid intake process and in which condition the first piston pump 111 should be at the beginning of the liquid intake process under target conditions. Hence, a potential discrepancy between a real piston status and a target piston status, the latter being defined by data stored in a target database 178, may be analyzed. Such a discrepancy of piston behavior in relation to the liquid motion may then be at least partly compensated for by the control unit 174 by performing a corresponding correction in control of the liquid supply system. The control can be adapted so that the metering scheme is maintained, but phase and/or duty cycle relation between the performance of the proportioning valve 108 and the first piston pump 111 may be modified. With the so-derived control information, the control unit 174 then controls both the proportioning valve 108 and the first piston pump 111.

Figure 2A:
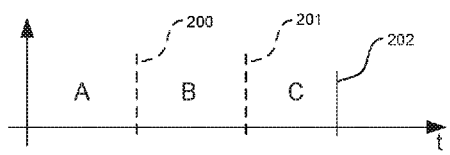
FIGS. 2A and 2B show how different solvents are drawn in during an intake phase of the pumping unit.

FIG. 2A shows an example of three different solvents A, B, C being drawn into the first pump chamber 117 during the first piston's downward stroke in accordance with a given metering scheme. Initially, the first liquid supply line 104 is connected to the pumping unit's inlet, and solvent A is drawn into the first pump chamber 117. After the first piston 115 has drawn in a certain amount of solvent A, the proportioning valve 108 switches from solvent A to solvent B at a point of time 200. Next, a certain amount of solvent B is drawn in via the second liquid supply line 105. At a point of time 201, the proportioning valve 108 switches from solvent B to solvent C. Then, a certain amount of solvent C is drawn into the first pump chamber 117. The point of time 202 indicates the end of the first piston's downward stroke. When the points of time 200, 201 are controlled in a coordinated manner, then at the end of the first piston's downward stroke, a defined solvent composition of solvents A, B, C is contained in the first pump chamber 117.

Figure 2B:
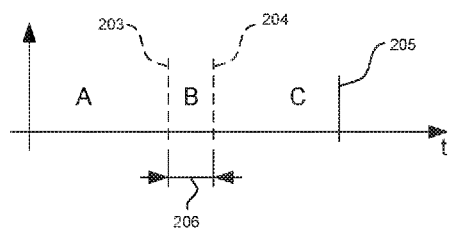

FIG. 2B shows another example where a large percentage of solvent A is mixed with a small percentage of solvent B in accordance with another given metering scheme. In this case, switching of the proportioning valve 108 is performed as follows: first, a certain amount of solvent A is drawn in. Then, at a point of time 203, the proportioning valve 108 switches from solvent A to solvent B, and a small amount of solvent B is drawn in. Then, at a point of time 204, the proportioning valve 108 switches back from solvent B to solvent A, and during the remaining part of the downward stroke, solvent A is drawn in. At the end of the first piston's downward stroke, at the point of time 205, the first pump chamber 117 contains a composite solvent comprising a large percentage of solvent A and a small percentage of solvent B.

It should be mentioned, that modes including indrawing of multiple packages of one and the same solvent during one intake stroke are also possible. E.g. in the FIGS. 2A, 2B the solvent A might be taken in instead of the solvent C in the interval 204-205, thus providing two packages of solvent A per stroke.

During the downward stroke of the first piston 115, the second piston 118 performs an upward stroke and delivers a flow of fluid, and at the pumping unit's outlet 121, a flow of composite solvent at high pressure is provided.

After the respective amounts of different solvents have been drawn into the first pump chamber 117, the inlet valve 113 is shut, the first piston 115 starts moving in the upward direction and compresses the liquid contained in the first pump chamber 117 to system pressure. In an alternative construction, when the proportioning valve 108 is capable to withstand high pressure, an extra inlet valve 113 may be omitted. The outlet valve 114 opens, and during the following refill phase, the first piston 115 moves in the upward direction, the second piston 118 moves in the downward direction, and the composite solvent is transferred from the first pump chamber 117 to the second pump chamber 120. During the refill phase, the amount of composite solvent supplied by the first piston pump 111 exceeds the amount of composite solvent drawn in by the second piston pump 112, and hence, at the outlet 125, a continuous flow of composite solvent is maintained.

After a well-defined amount of composite solvent has been supplied from the first piston pump 111 to the second piston pump 112, the outlet valve 114 is shut, the second piston 118 moves in the upward direction, thus a continuous flow of composite solvent is maintained, while the first piston 115 starts moving in the downward direction, the inlet valve 113 is opened, and again different solvents are drawn into the first pump chamber 117.

Figure 3:
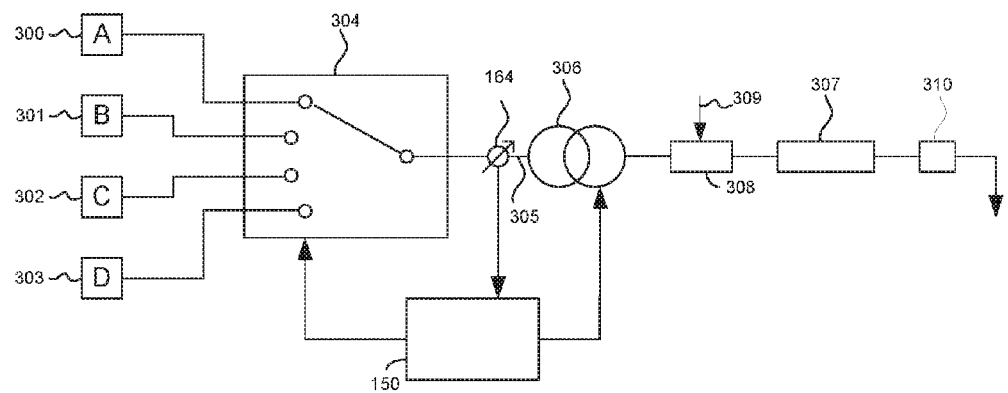
FIG. 3 gives an overview of a liquid chromatography system.

The fluid supply system shown in FIG. 1A, FIG. 1B may for example be used for supplying a flow of composite solvent to a separation device adapted for separating components of a sample liquid. FIG. 3 depicts the setup of a sample separation system. The sample separation system comprises four reservoirs 300 to 303 containing four different solvents A, B, C, D, which are fluidically coupled with a proportioning valve 304. The proportioning valve 304 is responsible for switching between different solvents and for providing the respective solvents to an inlet 305 of the pumping unit 306 at the low-pressure side of the pumping unit 306. The different solvents are thus brought together at the low pressure side of the pumping unit 306. The pumping unit 306 is configured to supply a flow of composite solvent to a separation device 307, which may for example be a chromatographic column. A sample injector 308 is located between the pumping unit 306 and the separation device 307. By means of the sample injector 308, a sample liquid 309 may be introduced into the separation flow path. The flow of composite solvent supplied by the pumping unit 306 drives the sample through the separation device 307. During passage through the separation device 307, the components of the sample are separated. A detection unit 310 located downstream of the separation device 307 is configured to detect the various components of the sample as they appear at the outlet of the separation device 307.

In the shown embodiment, only one event detection sensor 164 (which is e.g. a pressure sensor) is arranged in a conduit 305 between the proportioning valve 304 and the pumping unit 306. Similar as in FIG. 1A and FIG. 1B, a processor 150 analyzes the sensor signal of the sensor 164 only qualitatively to determine the beginning of a liquid intake process. Based on this information, the piston position in the pumping unit 306 is determined at the beginning of the liquid intake process. This information is, in turn, used to coordinate or adjust operation of proportioning valve 304 and pumping unit 306.

The fluid supply system shown in FIG. 1A, FIG. 1B is well-suited for being used in a liquid separation system, for example in a liquid chromatography system. It is to be noted, however, that the fluid supply system shown in FIG. 1 may be used in other fields as well.

Figure 4:
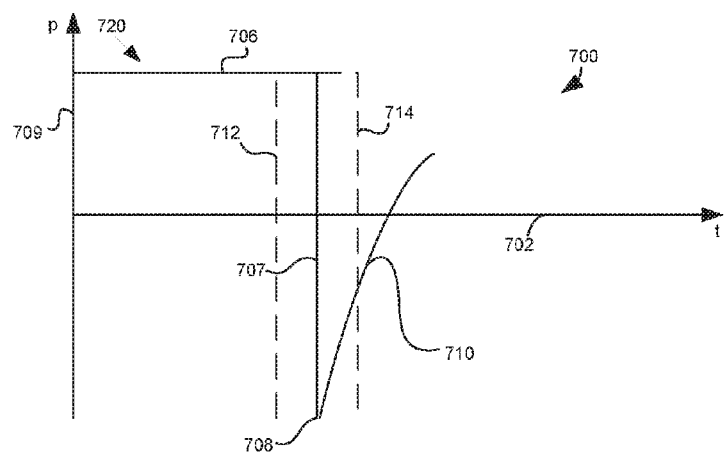
FIG. 4 shows pressure as a function of time around a beginning of a fluid intake process, wherein an impact of artifacts is shown as well.

FIG. 4 shows a diagram 700 having an abscissa 702 along which the time is plotted, whereas a pressure value as measured by a pressure sensors of a fluid supply system is plotted along an ordinate 704. The course of the pressure trace 720 is plotted in the diagram 700 of FIG. 4. The shown characteristic depicts a possible pressure signal of the sensor 164 starting at the phase in the duty cycle of the fluid supply system, at which a piston is close to the beginning of a fluid intake process. Following a region of constant pressure, compare reference numeral 706 (liquid in quiescent state), a sudden pressure drop occurs at the position 707. A point of time at which the fluid intake process starts at the piston is indicated by the onset of the pressure drop 707. After having passed through the minimum 708 the pressure increases again along curved line 710. The sensors may now, in combination with the analysis entity, detect the position of the onset of the pressure drop 707 as the point of time at which the fluid intake process begins.

Curve 720 relates to an ideal process. It may happen under real conditions that the actual pressure characteristic is shifted to lower values, compare reference numeral 712, due to artifacts, such as a leak in the fluid supply system or an adiabatic expansion of the fluid upon retracting the piston. It may also happen that the pressure characteristic is shifted towards higher values, see reference numeral 714, for instance as a result of compressibility of fluid at very high pressure values or the presence of gas bubbles in the liquid. Thus, the mentioned and other artifacts may have the effect that the actually determined moment of the beginning of the fluid intake process is not completely predictable and deviates from the expectation. An embodiment of the disclosed invention allows to exactly detect the beginning of the fluid intake and take corrective or adjusting measures to compensate for the discrepancy between the actual and ideal (expected) behavior.

In an embodiment, the control unit of FIG. 1A, FIG. 1B may consider such artifacts for a more precise control of the fluid supply system and/or to improve the precision and accuracy of sample separation results such as chromatogram, which is usually adversely affected by inaccuracies caused by such artifacts. To at least partially compensate for such artifacts, the control unit may model at least one artifact and its influence on the course of the sensor signal. The control unit may then correct the course of the sensor signal by at least partially compensating the influence of the at least one artifact on the course of the sensor signal. Therefore, the derived necessary corrective/adjusting action may become even more precise by taking the influence of such artifacts in consideration, as described.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A fluid supply system configured for metering two or more fluids in controlled proportions in accordance with a given metering scheme and for supplying a resultant mixture, the fluid supply system comprising:
   a plurality of solvent supply lines, each fluidically connected with a fluid source providing a respective fluid;
   a pumping unit comprising an inlet, an outlet, and a reciprocating element configured for intaking fluid supplied at the inlet and for supplying the pressurized fluid at the outlet, wherein the pumping unit is configured for taking in fluids from selected solvent supply lines and for supplying a pressurized mixture of the fluids at the outlet;
   a proportioning valve interposed between the solvent supply lines and the inlet, the proportioning valve configured for modulating solvent composition by sequentially coupling selected ones of the solvent supply lines with the inlet;
   a sensor configured for sensing process information in the fluid supply system relating to a fluid intake process of the pumping unit;
   an analysis entity configured for analyzing the sensed process information and for determining as a result of the analysis, independently of a position of the reciprocating element within the pumping unit, the event of the beginning of a fluid intake process, wherein the analysis entity is further configured for determining reciprocating element related information at the event of the beginning of the fluid intake process; and
   a control unit configured for switching the proportioning valve to sequentially couple selected ones of the solvent supply lines to the inlet of the pumping unit at one or more switching points during a duty cycle of the reciprocating element coordinated with the motion of the reciprocating element based on the given metering scheme and based on the reciprocating element related information,
   wherein the control unit is configured for coordinating operation of the pumping unit and the proportioning valve for at least partially compensating for a discrepancy between an actual relationship between operation of the pumping unit and the proportioning valve, as indicated by the reciprocating element related information determined by the analysis entity, and a target relationship between operation of the pumping unit and the proportioning valve, as predefined for operating the fluid supply system.

2. The fluid supply system of claim 1, wherein the analysis entity is configured for analyzing the sensed process information in terms of at least one predefined artifact criterion for determining at least one artifact feature in the sensed process information, and is configured for analyzing a relation between the at least one predefined artifact feature and the determined reciprocating element related information.

3. The fluid supply system of claim 2, wherein the at least one predefined artifact criterion comprises at least one of the group consisting of an influence of gas bubbles in the fluid, an influence of leakage in the fluid supply system, an influence of compressibility of the fluid, a volume contraction resulting from a mixing of multiple components of the fluid, an influence of a temperature of the fluid, a thermal effect of mixing of different fluids, and an influence of adiabatic expansion of the fluid.

4. A sample separation system for separating components of a sample fluid in a mobile phase, the sample separation system comprising:
    a fluid supply system according to claim 1, the fluid supply system being configured to drive the fluid as the mobile phase through the sample separation system; and
    a separation unit configured for separating components of the sample fluid in the mobile phase.

5. The sample separation system of claim 4, further comprising at least one of:
    a sample injector configured to introduce the sample fluid into the mobile phase;
    a detector configured to detect separated components of the sample fluid;
    a collection unit configured to collect separated components of the sample fluid;
    a data processing unit configured to process data received from the sample separation system; and
    a degassing apparatus for degassing the mobile phase.

6. The fluid supply system of claim 1, further comprising at least one of:
    during an intake movement of the reciprocating element, when fluid is drawn in via the inlet, or between intervals during which the fluid is drawn in via the inlet, the proportioning valve performs switching between different solvent supply lines;
    the proportioning valve comprises a plurality of switching valves, with the switching valves being sequentially actuated during an intake movement of the reciprocating element of the pumping unit;
    the proportioning valve comprises at least one multi-port selection valve;
    the proportioning valve is configured for selecting a selected one of the solvent supply lines corresponding to a multiplexer scheme; and
    predefined portions of an intake movement of the reciprocating element are assigned to different solvents that are drawn into the pumping unit, wherein proportioning is done by metering of one of volumetric packets, time slices, and position of the reciprocating element.

7. The fluid supply system of claim 1, wherein the sensor is arranged hydraulically at at least one of the following positions:
    a position between the proportioning valve and the pumping unit;
    a position within the solvent supply lines;
    a position within the proportioning valve;
    a position upstream of an intake valve arranged directly upstream of the pumping unit; and
    a position within an intake valve arranged at a low pressure side of the pumping unit.

8. The fluid supply system of claim 1, comprising at least one of:
    the control unit is configured for coordinating operation of the pumping unit and the proportioning valve for at least partially compensating for a potential discrepancy between an actual fluid motion on the intake side of the pumping unit resulting from a relationship between operation of the pumping unit and the proportioning valve, as indicated by the determined reciprocating element related information, and a target motion of the fluid as desired based on a target relationship between operation of the pumping unit and the proportioning valve, as predefined for operating the fluid supply system;
    the control unit is configured for controlling operation of the fluid supply system to at least partially compensate for at least one of a steering inaccuracy, a mechanical inaccuracy, and a non-ideal valve function;
    the control unit is configured for controlling operation of the fluid supply system in accordance with at least one of the group consisting of the sensed process information, fluid intake information relating to the event of the beginning of the fluid intake process, and the reciprocating element related information;
    the control unit is configured for controlling fluid intake by the pumping unit based on the reciprocating element related information to adjust a size of an initial fluid packet to be taken in during the intake process;
    the control unit is configured for controlling fluid intake by the pumping unit based on the reciprocating element related information to adjust a size ratio of the fluid packets to be taken in during the intake process;
    the control unit is configured for controlling fluid intake by the pumping unit based on the reciprocating element related information to adjust a ratio of total amounts of each solvent taken in during the intake process;
    the control unit is configured for controlling fluid intake by the pumping unit based on the reciprocating element related information to correct a size of fluid packets taken in by the pumping unit;
    the control unit is configured for controlling fluid intake by the pumping unit based on the reciprocating element related information to adjust a size of an initial fluid packet to be taken in during the intake process in accordance with its relation to the size of other packets;
    the control unit is configured for controlling operation of the fluid supply system for at least partially compensating a potential discrepancy between target reciprocating element related data and the determined actual reciprocating element related information; and
    the control unit is configured for adjusting, based on the determined reciprocating element related information, a future motion profile in accordance with which the reciprocating element is moved in the pumping unit.

9. The fluid supply system of claim 1, comprising at least one of the following features:
    the sensor comprises one of the group consisting of a pressure sensor, a flow sensor, an acoustic sensor, a temperature sensor, a sensor configured for determining a change in a motion state of the fluid, and a sensor configured for sensing a change in fluid flow properties of the fluid;
    the fluid supply system comprises a plurality of sensors arranged at different positions in the fluid supply system;

the fluid supply system comprises at least one sensor arranged at a position between the proportioning valve and the pumping unit, and at least one other sensor arranged at a position within at least one of the plurality of solvent supply lines.

10. The fluid supply system of claim 1, wherein the reciprocating element related information is indicative of one of reciprocating element state information, process state information, time information, phase information of the operation cycle of the reciprocating element, a point of time at which the fluid intake process begins, and a spatial position of the reciprocating element within a pumping chamber of the pumping unit at the beginning of the fluid intake process.

11. The fluid supply system of claim 1, wherein the analysis entity is configured for analyzing at least one of the groups consisting of:
    a course of a pressure trace, as the sensed process information for determining the reciprocating element related information;
    a derivative of a time-dependent pressure trace over time, as the sensed process information for determining the reciprocating element related information; and
    a mathematical function derived from a pressure trace, as the sensed process information for determining the reciprocating element related information.

12. The fluid supply system of claim 1, wherein the analysis entity is configured for determining the reciprocating element related information based on a position of a peak value of a course of a pressure trace, or of the derivative of the pressure trace, or of a mathematical function derived from the pressure trace.

13. The fluid supply system of claim 1, wherein the reciprocating element is a first reciprocating element, and the pumping unit further comprises a second reciprocating element configured for displacing, in cooperation with the first reciprocating element, the fluid supplied at the inlet and for supplying the fluid further pressurized at the outlet.

14. The fluid supply system of claim 1, wherein the pumping unit is a first pumping unit and the reciprocating element is a first reciprocating element, and further comprising a second pumping unit arranged downstream of the first pumping unit, the second pumping unit comprising a second reciprocating element and configured for displacing, by the second reciprocating element, the fluid supplied at the outlet of the first pumping unit and at an inlet of the second pumping unit and for supplying the fluid further pressurized at an outlet of the second pumping unit.

15. The fluid supply system of claim 1, wherein the pumping unit is a first pumping unit and the reciprocating element is a first reciprocating element, and further comprising a further second pumping unit arranged hydraulically parallel to the first pumping unit, the second pumping unit comprising a second reciprocating element and configured for displacing by the second reciprocating element in alternating manner together with the first pumping unit, the fluid supplied from the proportioning valve.

16. The fluid supply system of claim 1, wherein the control unit is configured for switching the proportioning valve using the given metering scheme and based on the reciprocating element related information for synchronizing or for adjusting synchronization of a proportioning valve duty cycle with a pumping unit duty cycle.

17. A method of metering two or more fluids in controlled proportions in accordance with a given metering scheme and of supplying a resultant mixture, wherein each of a plurality of solvent supply lines is fluidically connected with a fluid source providing a respective fluid, the method comprising:
    controlling a pumping unit comprising a reciprocating element for displacing fluid supplied at an inlet of the pumping unit and for supplying the pressurized fluid at an outlet of the pumping unit, wherein the pumping unit takes in fluids from selected solvent supply lines and supplies a pressurized mixture of the fluids at the outlet;
    modulating solvent composition by a proportioning valve, which is interposed between the solvent supply lines and the inlet, by sequentially coupling selected ones of the solvent supply lines with the inlet;
    sensing process information relating to a fluid intake process of the pumping unit;
    analyzing the sensed process information and determining as a result of the analysis the event of the beginning of a fluid intake process, independently of a position of the reciprocating element within the pumping unit;
    determining reciprocating element related information at the event of the beginning of the fluid intake process;
    switching the proportioning valve to sequentially couple selected ones of the solvent supply lines to the inlet at one or more switching points based on the given metering scheme and based on the reciprocating element related information; and
    coordinating operation of the pumping unit and the proportioning valve for at least partially compensating for a discrepancy between an actual relationship between operation of the pumping unit and the proportioning valve, as indicated by the reciprocating element related information determined by the analysis entity, and a target relationship between operation of the pumping unit and the proportioning valve, as predefined for operating the fluid supply system.

18. A software program or product, stored on a non-transitory data carrier, for controlling or executing the method of claim 17, when run on a data processing system.

19. A fluid supply system, comprising:
    a pumping unit comprising an inlet, an outlet, and a reciprocating element configured for displacing a fluid supplied at the inlet and for supplying the pressurized fluid at the outlet;
    a sensor configured for sensing process information in the fluid supply system relating to a fluid intake process of the pumping unit;
    an analysis entity configured for analyzing the sensed process information for determining fluid intake information indicative of the beginning of the fluid intake process, and for determining as a result of the analysis the event of the beginning of the fluid intake process independently of a position of the reciprocating element within the pumping unit, wherein the analysis entity is configured for determining reciprocating element related information corresponding to the occurrence of the beginning of the fluid intake process;
    a proportioning valve configured for modulating solvent composition by sequentially coupling selected solvent supply lines with the inlet; and
    a control unit configured for coordinating operation of the pumping unit and the proportioning valve for at least partially compensating for a discrepancy between an actual relationship between operation of the pumping unit and the proportioning valve, as indicated by the reciprocating element related information determined by the analysis entity, and a target relationship between operation of the pumping unit and the proportioning valve, as predefined for operating the fluid supply system.

20. A method, comprising:

controlling a pumping unit comprising a reciprocating element for displacing a fluid supplied at an inlet of the pumping unit and for supplying the pressurized fluid at an outlet of the pumping unit;

modulating solvent composition by a proportioning valve to sequentially couple selected solvent supply lines with the inlet;

sensing process information relating to a fluid intake process of the pumping unit;

analyzing the sensed process information for determining fluid intake information indicative of the beginning of the fluid intake process, and determining as a result of the analysis the event of the beginning of the fluid intake process independently of a position of the reciprocating element within the pumping unit;

determining reciprocating element related information corresponding to the occurrence of the beginning of the fluid intake process; and coordinating operation of the pumping unit and the proportioning valve for at least partially compensating for a discrepancy between an actual relationship between operation of the pumping unit and the proportioning valve, as indicated by the reciprocating element related information determined by the analysis entity, and a target relationship between operation of the pumping unit and the proportioning valve, as predefined for operating the fluid supply system.

21. A method, comprising:

controlling a pumping unit comprising a pumping chamber having a reciprocating element disposed therein for displacing fluid supplied at an inlet of the pumping unit and for supplying the pressurized fluid at an outlet of the pumping unit, wherein the pumping unit takes in fluids from selected solvent supply lines and supplies a pressurized mixture of the fluids at the outlet;

modulating solvent composition by sequentially coupling selected ones of the solvent supply lines with the inlet of the pumping unit via a proportioning valve which is interposed between the solvent supply lines and the inlet of the pumping unit;

sensing process information relating to a fluid intake process of the pumping unit;

analyzing the sensed process information, and determining as a result of the analysis, independently of a position of the reciprocating element within the pumping unit, the event of the beginning of a fluid intake process;

determining a position of the reciprocating element within the pumping chamber at the event of the beginning of the fluid intake process;

switching the proportioning valve to sequentially couple selected ones of the solvent supply lines to the inlet of the pumping unit at one or more switching points which are selected based on the determined position of the reciprocating element within the pumping chamber at the event of the beginning of the fluid intake process; and coordinating operation of the pumping unit and the proportioning valve for at least partially compensating for a discrepancy between an actual relationship between operation of the pumping unit and the proportioning valve, as indicated by the reciprocating element related information determined by the analysis entity, and a target relationship between operation of the pumping unit and the proportioning valve, as predefined for operating the fluid supply system.

* * * * *